United States Patent [19]
Kim

[11] 4,358,629
[45] Nov. 9, 1982

[54] METHOD OF PRODUCING ACETYLENE FROM COAL

[75] Inventor: Chi S. Kim, Cambridge, Mass.

[73] Assignee: Avco Corporation, Wilmington, Mass.

[21] Appl. No.: 179,144

[22] Filed: Aug. 18, 1980

[51] Int. Cl.³ .................. C10B 49/02; C10B 49/08; C10B 51/00
[52] U.S. Cl. .................. 585/538; 585/241; 585/537; 585/539; 208/8 R; 204/171
[58] Field of Search .............. 585/538, 537, 539, 241; 208/8 R

[56] References Cited

U.S. PATENT DOCUMENTS

| | | | |
|---|---|---|---|
| Re. 25,218 | 8/1962 | Schallus et al. | 585/538 |
| 1,757,454 | 5/1930 | Eisenhut | 204/171 |
| 2,080,767 | 5/1937 | Dreyfus | 208/8 R |
| 3,217,056 | 11/1965 | Sennewald et al. | 585/537 |
| 3,384,467 | 5/1968 | Ammann et al. | 585/534 |
| 3,395,194 | 7/1968 | Keckler et al. | 585/539 |
| 4,010,090 | 3/1977 | Fey et al. | 204/171 |
| 4,105,888 | 8/1978 | Fey | 585/539 |

FOREIGN PATENT DOCUMENTS

| | | | |
|---|---|---|---|
| 455567 | 10/1936 | United Kingdom | 585/539 |
| 1068552 | 5/1967 | United Kingdom | 585/539 |

OTHER PUBLICATIONS

Kawana et al., "Acetylene from Coal by Hydrogen Plasma", pp. 1657–1661 (1967), *Kogyo Kagaku Zasshi* 70(10) (Chem. Abst. 68:42128g).

Chakravarty et al., "Reaction of Coals Under Plasma Conditions", *Fuel* 55(1) pp. 43–46 (1976) (Chem. Abst. 85:8053v).

Gannon, et al., "Arc-Coal Process Development", *Govt. Rep. Announce.* 74(23), 1974 (Chem. Abst. 82:173373v).

Stanislaw, et al., "Gasification of Coal . . . with a Spouted Bed", *Koks, Smola, Gaz.*, pp. 123–128 (1971) (Chem. Abst. 75:119904m).

*Primary Examiner*—Curtis R. Davis
*Assistant Examiner*—Olik Chaudhuri
*Attorney, Agent, or Firm*—Abraham Ogman

[57] ABSTRACT

This invention relates to the conversion by way of decomposing a solid carbonaceous matter to acetylene. Specifically, the invention teaches selecting the operating conditions which will produce high yield at low cost. Specific values of heat and enthalpy for the carbonaceous matter and the gas are proposed in combination with specific particle sizes and reaction time. All of the foregoing contribute to producing acetylene at a commercially competitive cost.

13 Claims, 5 Drawing Figures

METHOD OF PRODUCING ACETYLENE FROM COAL

TECHNICAL FIELD

This invention relates to an energy efficient process for decomposing solid carbonaceous matter with volatile content to produce a high yield of acetylene at relatively low cost.

DEFINITIONS

The term "solid carbonaceous matter" is intended to define a class of materials where the hydrogen to carbon atom ratio is 0.3 to 2.0 with a volatile content. The preferred carbonaceous matter is coal. However, lignite, peat, plastic and others will also qualify.

The term "volatile" is hereby defined as compositions which separate from the carbonaceous matter when tested. For example, coal and coke are analyzed pursuant to ASTM Designation D271-64. This analysis is widely recognized as "proximate" analysis.

BACKGROUND OF PRIOR ART

Historically, the conversion of coal and other carbonaceous matter to acetylene by means of electric arc heaters, and in particular other heating devices, are well-known.

Conventionally, carbonaceous matter, together with hydrogen, are heated by an electric arc device or other suitable source of heat. The mixture is heated so that the carbonaceous matter decomposes. The composition that is produced as a result of the decomposition of the carbonaceous matter will depend on the reaction conditions existing in the decomposition or reaction zone. It is well-known that the formation of certain compositions are favored under specified reaction conditions. For example, the formation of acetylene as an intermediate product is favored where the temperature of the reaction zone is above 1300 K. The formation of acetylene relative to the simultaneous decomposition of acetylene is also favored at or near 1300 K.

In U.S. Pat. No. 1,757,454, there is a process whereby water vapor is employed as the suspension agent for coal dust. The combination is fed to an electric arc where a chemical reaction produces acetylene.

Another arc coal/acetylene conversion process is described in U.S. Pat. No. 2,916,534, which was reissued as RE 25,218. The process described in this patent makes use of hot hydrogen molecules which are partly or totally dissociated into atoms to decompose hydrocarbons. This patent also specifies a specific flow rate of hydrogen gas through the reaction zone and also the mole ratio of gas to carbon in the hydrocarbons.

U.S. Pat. No. 3,217,056 is another patent which utilizes the heat available in atomic hydrogen to decompose carbonaceous matter. The heat content of the hydrogen gas and also reaction times are specified.

U.S. Pat. No. 4,010,090 makes use of a hydrocarbon gas stream to increase the length of an arc before coal or other carbonaceous matter is provided to the arc. The principal virtue of this patent relative to the invention is the large number of other patents relative to arc reactors disclosed in column 2, lines 11-17.

U.S. Pat. No. 3,395,194 describes a partial oxidation process using an electric arc device to heat a gaseous hydrocarbon in the presence of oxygen and at very high pressures.

Generally, where an electric arc is used as a heat source, the electric arc passes through the hydrogen gas causing the gas to increase in temperature to extremely high temperatures in a very short time. Arc column temperatures commonly reach 8,000 K to 20,000 K. The gas, on leaving the arc and entering the reaction zone, is commonly within the neighborhood of 2,000–5,000 K. Under these conditions, the hydrogen molecules may dissociate partially into hydrogen atoms.

Once the hydrogen leaves the arc, there is an extremely rapid tendency for the hydrogen atoms to recombine into molecules, and in doing so, they give off tremendous amounts of heat. A portion of this heat, in addition to the sensible heat of the gas, is absorbed by the coal particle, mostly via conduction, convection and radiation, thereby causing the coal particle to decompose and more specifically to give off its volatile content, i.e., to devolatize.

It is also well-known and established that process steps and conditions will vary greatly with the type of carbonaceous matter fed to the arc. Heretofore, gaseous and liquid carbonaceous matter were the favored feestocks, as there was no known way of producing a high yield of acetylene at reasonable costs from solid carbonaceous matter. Also gaseous and liquid feedstocks were easier to handle and produced less wear and tear on the arc apparatus.

Thus in summary though the basic process steps are known, it is hypothesized that the mechanics and the kinetics of the process, for example, were not understood well enough, heretofore, to teach one how to maximize the yield of acetylene from solid carbonaceous matter in an energy efficient manner.

The following description represents an understanding of the process directed specifically to solids having volatile content. The necessary process parameters are provided for heating the solid particles as fast as possible to decompose the particle forming volatiles as fast as possible so as to avoid the char forming secondary reactions of these volatiles in the solid particles.

With due recognition of the prior art:

It is an object of the invention to provide a process for converting solid carbonaceous matter into acetylene by decomposing the carbonaceous matter under specific process conditions.

It is yet another object of the invention to describe a process wherein the enthalpies of the source of gaseous heat and heat enthalpies of the carbonaceous matter are adjusted within a specified range in order to increase the yield of acetylene.

It is another object of the invention to perform the process of decomposing solid carbonaceous matter within an electric arc apparatus.

It is yet another object of the invention to provide operating conditions in an electric arc reactor for decomposing solid carbonaceous matter for the production of acetylene.

It is still another object of the invention to provide a process which removes a least 25 percent of the volatiles from solid carbonaceous matter before the carbonaceous matter leaves the reaction zone.

In accordance with the invention, a process is described whereby acetylene is produced from solid carbonaceous matter by decomposing the carbonaceous matter in hydrogen in a reaction where the specific gas enthalpy and the specific carbonaceous matter enthalpy are tightly controlled. In addition, the size of the particles of carbonaceous matter is maintained below a specific minimum in order to cause the removal of more than 25 percent of the volatiles present in the carbonaceous matter within the time it takes the coal and gas to pass through the reaction zone.

The novel features that are considered characterisitc of the invention are set forth in the appended claims; the invention itself, however, both as to its organization and method of operation, together with additional objects and advantages thereof, will best be understood from the following description of a specific embodiment, when read in conjunction with the accompanying drawings, in which:

DESCRIPTION OF THE INVENTION

The invention is applicable broadly to solid carbonaceous matter such as coal, lignite, plastics, etc. However, the following discussion will be limited to coal in order to simplify matters.

If one were to plot the SER as a function of the specific gas enthalpy and a function of the coal loading (carbon content of coal per hour per standard cubic foot per minute of hydrogen), it would be noted that the production of acetylene from carbonaceous matter or coal is heavily dependent on operating parameters. The dependency of the SER and yield also changes as a function of the reaction temperature. The crux of this invention, therefore, is to pinpoint the operating parameters which will result in producing high yields of acetylene at low values of SER.

Figure 1:
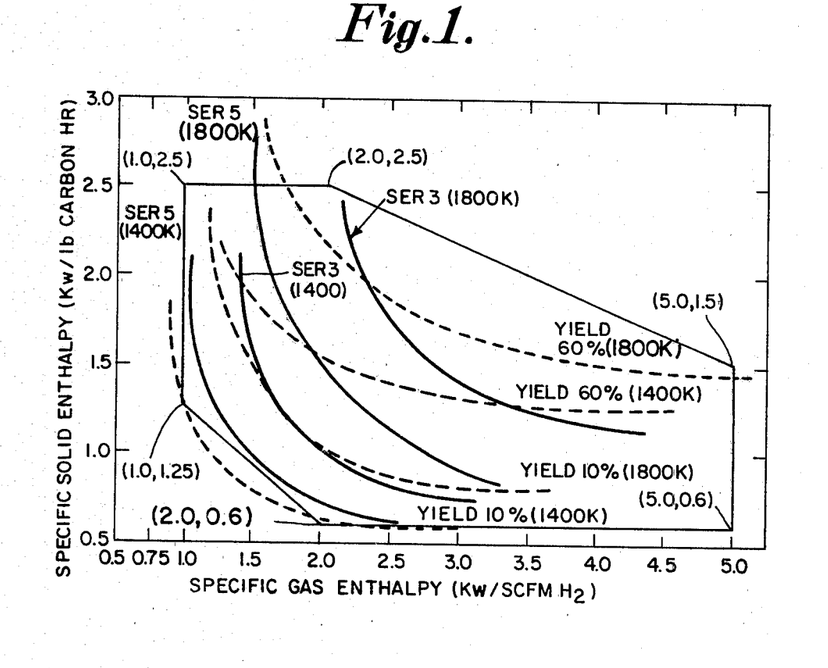
FIG. 1 is a series of curves showing SER (Specific Energy Requirement, Kwhr/lb $C_2H_2$ produced) and acetylene yield as functions of specific solid enthalpy and specific gas enthalpy at various "frozen" product temperatures, the "frozen" product temperature being defined as the temperature of the product stream just before a primary quench.

FIG. 1 is a plot of iso-yield curves and iso-SER curves for two values of "frozen" product temperature plotted on the coordinates of specific gas enthalpy vs. specific solid enthalpy. The latter is defined as power input in Kw per pound carbon flow per hour. The Figure contains lines of SERs of three and five and acetylene yields of 10 percent and 60 percent at "frozen" product temperatures of 1400 K and 1800 K. The curves show that a low SER can be attained even with a relatively low acetylene yield at the lower temperature. Likewise, a low SER can be attained even at the high "frozen" product temperature if the acetylene yield is high. The respective enthalpies are adjusted by regulating the electric power, gas feed rate and coal feed rate.

The "frozen" product temperature may, more or less, be regulated by controlling the reaction time. They are not merely an independent process parameter, but depend on the input condition of other process parameters. They also depend on physical and chemical characteristics of the feed materials and the reaction system; for example, coals of different composition will undergo different time-temperature history under otherwise identical input conditions because they will experience different time-product composition history. The maximum "frozen" temperature can be as high as the system permits, but in order to maintain low SERs with realistic yields, the temperature cannot be much higher than 1800 K.

The process under these conditions proceeds more efficiently at relatively low pressures, e.g., under 2 atmospheres.

It is possible from the above consideration and from FIG. 1 to define an envelope for coal, power, and hydrogen flow rates in terms of specific gas and solid enthalpies. Assume the lower left half of the boundary of the envelope is determined by the SER of five at 1400 K and the upper right half by the acetylene yield of 60 percent at 1800 K. The latter limit is chosen because acetylene yields cannot realisticly be more than 60 percent under any circumstances. The boundary is also drawn at the specific gas enthalpy of five and the specific solid enthalpy of 2.5 because they are too far removed from the minimum SER operating conditions desired. The net result is an envelope which is defined by the lines joining the x, y coordinates (1.0, 2.5) (2.0, 2.5) (5.0, 1.5) (5.0, 0.6) (2.0, 0.6) (1.0, 1.25), where x is the specific gas enthalpy in Kw/SCFM $H_2$ and y is the specific solid enthalpy in Kw/lb carbon HR.

It is noted that the specific gas and solid enthalpies can also be expressed in metric units of K cal/g mole of gas and K cal/grams of carbon by multiplying 0.544 to Kw/SCFM and 1.896 to Kw/lb carbon per hour, respectively. The conversion may become useful in understanding the process energy requirements when the heat input is in the form of thermal energy instead of the electric energy.

It is also noted that in a commercial embodiment of this invention, the hydrogen would be recovered from the product stream and recycled in the process. Therefore, the feed hydrogen may contain other gaseous species such as carbon monoxide, water vapor, and hydrocarbons, which may have been produced as by-products in the process. In such a case the specific gas enthalpy noted above would be based on the total flow of gas including the contaminants.

The invention defined in FIG. 1, therefore, establishes the first set of operating parameters in this disclosure.

An analytical model was formulated. The model incorporates the basic thermochemistry and fluid dynamics that are obviously important in the complex interactions within the high temperature reactor, and additionally includes certain constraints and assumptions necessary to be consistent with observed results. The capability to predict the effect of changes in independent process variables on the critical output parameters makes the model valuable in directing process improvement experiments, as well as in scaling the reactor to larger capacities.

Figure 2:
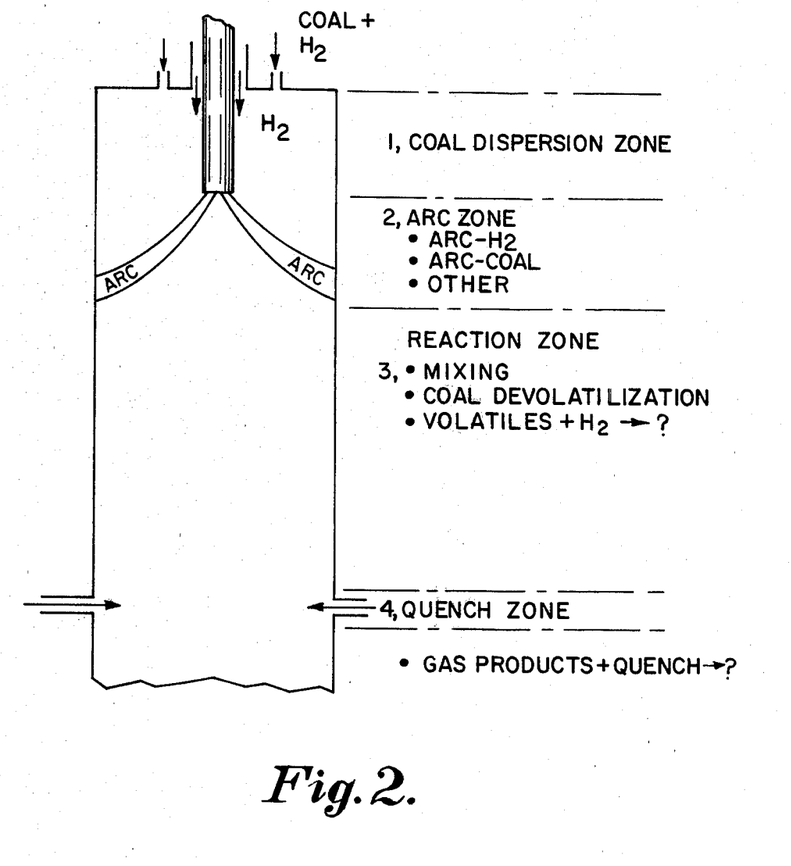
FIG. 2 is a schematic representation of an electric arc reactor.

In the formulation of the model the arc coal reactor was conceptually divided into four zones, as indicated by the simplified diagram in FIG. 2. Owing to the complex fluid dynamic and thermochemical processes occurring in the reactor during its operation, it is necessary to recognize only those processes which have a first-order effect on the quantity of acetylene produced, thereby simplifying the modeling to a more tractable format. This is done by making the following plausible assumptions.

In the coal dispersion zone, the most important process is the mixing of the coal-hydrogen feed with the main stream hydrogen. In this model, it is assumed that all coal particles are uniformly dispersed in the hydrogen gas by the time the mixture enters the arc zone.

In the arc zone a rotating arc sweeps through the hydrogen-coal mixture. Because the arc follows the path of least resistance, it is reasonable to assume that this path is provided by the hydrogen gas rather than by a path linked through the coal particles. In other words, this assumption implies that the ionized conductivity of hydrogen is much higher than the conductivity of coal particles. Therefore, as the coal-hydrogen mixture passes through the arc zone, the electrical power input heats up only the hydrogen gas and not the coal particles. The particles, in turn, get heated by the hot hydrogen gas by conduction and convection. Because of the short residence time in the arc zone compared to that in the reaction zone, and also because of the thermal inertia of the coal particles, it is very likely that the coal particles remain essentially at their inlet temperature while the gas reaches its high temperature. In view of the foregoing, the most important assumption is that in the arc zone the hydrogen absorbs all of the input power and reaches a high temperature, which is determined from equilibrium considerations, while the temperature of the coal particles remains unaltered.

In the reaction zone the hot hydrogen gas heats the coal particles by conduction and convection. The particles pyrolyze, and the volatiles produced by pyrolysis mix and react with the hydrogen. The volatiles thus produced under this rapid heating condition are composed of species containing essentially hydrogen and carbon elements and resemble in structure various functional groups existing in the parent carbonaceous matter. Above 1400 K the hydrocarbon volatiles tend to further pyrolyze to acetylene and ultimately to carbon and hydrogen unless the reaction is quenched. Hydrogen is preferred as the reaction medium because of its high thermal conductivity compared with most other gases and its possible participation in the formation reaction of acetylene as it is a constituent of the molecule. It is also known that hydrogen tends to retard the decomposition of acetylene through inhibitory reaction mechanisms and by diluting the concentration of the molecule in the product gas.

Thermodynamic equilibrium computations for this reactive gas mixture indicate that the final composition comprises of predominantly condensed carbon and hydrogen. Evidently, acetylene forms through complex transient kinetic routes before this mixture reaches complete equilibrium.

Overall production of acetylene in the arc coal reactor is in essence a continual process of formation and decomposition of acetylene; the formation rate being somewhat higher than the decomposition rate. As a result, there always exists the optimum residence time at which the overall production of acetylene is maximum and hence the product stream should be quenched to maximize the net production of acetylene for the given input condition. In general the quench medium can be either purely thermal or both thermal and chemical (i.e., additional chemicals are produced from the quench medium by absorbing a portion of the sensible heat of the product stream). If it is a purely thermal quench, the composition of the quench is immaterial; only its thermal capacity to reduce the temperature is important, provided that the resulting acetylene concentration is not too low for economic separation and purification of acetylene. If it is both thermal and chemical, the composition of the quench is obviously significant. For the modeling purposes here, the quench is assumed to be purely thermal and perfect. That is, it is assumed that the composition of the hot products just prior to the quench is "frozen" instantaneously by the quench.

As the coal particles are heated by hot hydrogen, they decompose to produce volatiles through complex kinetic routes. The volatiles are essentially hydrocarbons which are unstable at elevated temperatures. New compounds are constantly being formed and decomposed as the temperature of the volatiles within the reaction zone decreases. If the reaction were permitted to go to thermal equilibrium, the coal would eventually form char, condensed carbon, soot, hydrogen, and small amounts of other hydrocarbon species. The purpose of the quench is to: prevent thermal equilibrium at elevated temperatures; and to reduce the reaction products leaving the reaction zone from a temperature which favors the production of acetylene to a much lower temperature at which acetylene is stable.

Thus the formation of acetylene is, in reality, an intermediate step in the thermal decomposition process. Though it is formed at favorable temperatures, the model and experiments show that acetylene yield reaches a peak for a certain optimum residence time. At longer residence times the yield decreases. The yield decreases because of the degradation of acetylene to soot and hydrogen that occurs simultaneously with its formation. This degradation process is sometimes called acetylene pyrolysis.

Figure 3:
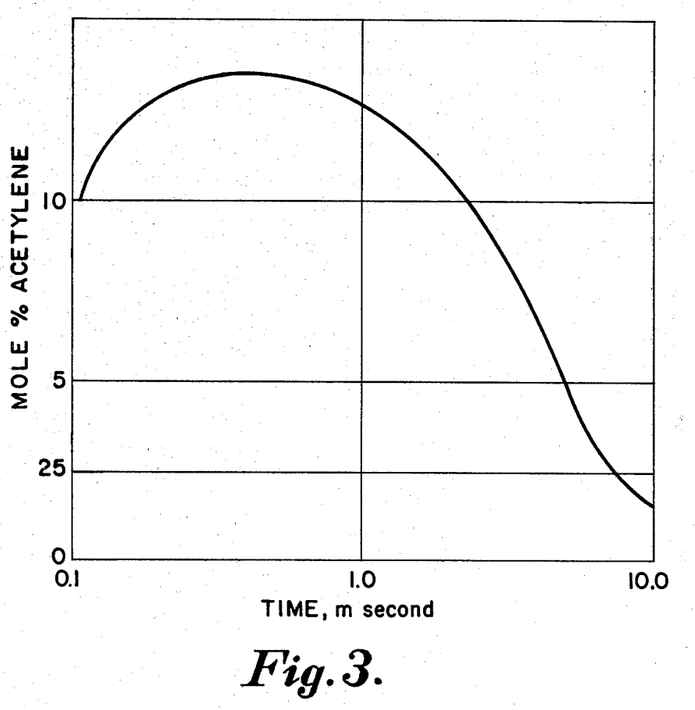
FIG. 3 is a curve of the mole percent of acetylene produced as a function of time at specific reaction temperatures.

FIG. 3 depicts a curve of mole percent of acetylene produced as a function of time. The magnitude of acetylene will change as the operating parameters of the process change; but the shape of the curve is a general one. The concentration yield of acetylene reaches a peak in less than one millisecond and remains high out to at least ten milliseconds. The concentration and thus the yield then drops off rapidly.

Having previously described and discussed the benefits of operating under specified solid and gas enthalpies, a second important operating parameter is established. The decomposition reaction should take place in about 0.5 milliseconds and should be completed in less than 10 milliseconds in order to maximize concentration and yield.

Previously, it was noted that as the coal particles heat up, they tend to decompose. It was also noted that the yield of acetylene is directly related to the volatile yield. It follows, therefore, that it will be necessary to achieve maximum decomposition in a time period of about 0.5 milliseconds, but in any event, less than ten milliseconds.

The arc-heated hydrogen is initially heated to high temperatures, but then rapidly cools as it heats and reacts with the coal particles. The coal particles, on the other hand, are heated until they achieve the gas temperature. Under conditions wherein the heat content or enthalpy of the gas and the coal operated within the envelope defined previously and shown in FIG. 1, it has been determined that particles smaller than 40 microns will reach the gas temperature in less than one millisecond, while larger particles heat more slowly producing less volatiles.

Figure 4:
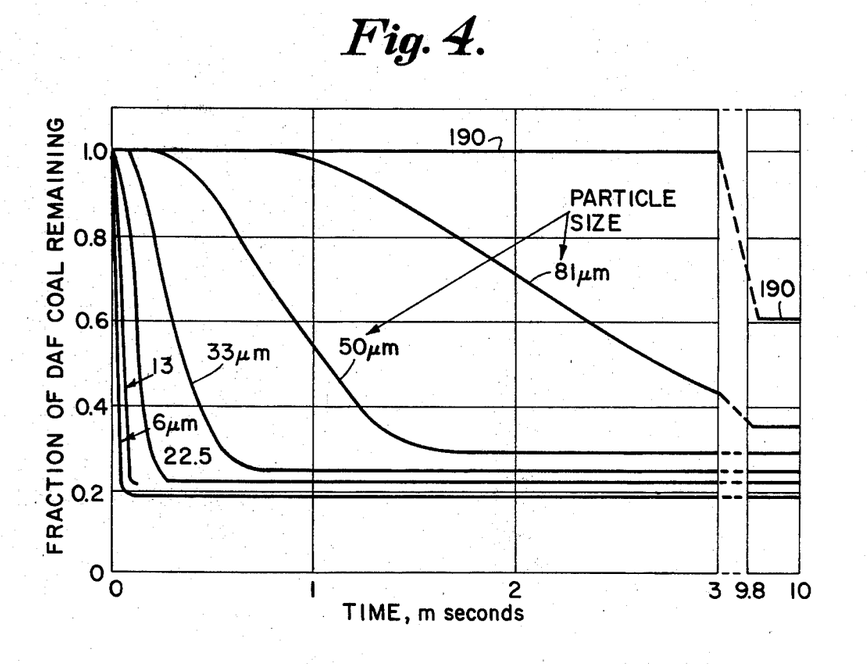
FIG. 4 is a curve of the fraction of coal mass remaining as a function of time as the coal has undergone decomposition within a reaction zone.

The relation between volatile yield and particle size is illustrated in FIG. 4. These curves are based on a specific coal sample where the volatile content was 40% based on the ASTM proximate analysis. Coal having 18% proximate volatile content or more is considered suitable for conversion to acetylene. A typical particle size distribution by weight is disclosed in the following examples. The data shows that particles below 33 microns in diameter yield close to the maximum of 80% of their original weight leaving 20% of their weight as remaining char. The larger particles yield progressively less volatiles for the larger sizes until, as the Figure shows, particles of about 190 microns only produce volatiles commensurate with the proximate analysis of the coal. In particular, it will be noted that there is a perfect correlation between the time interval needed for maximum acetylene yield and the time interval available for maximizing volatile yields if the coal particle size is maintained below 190 microns and preferably in the neighborhood of 25 to 50 microns.

Test data developed in test runs are provided in the following examples. Examples 1 and 2 define conditions outside of the envelope defined in FIG. 1. Examples 3 and 4 represent conditions within the envelope. The test data in Example 4 includes quenching.

EXAMPLE 1

A direct current electric arc reactor in which the d.c. arc was made to rotate at 1000–3000 revolutions per second by the action of an external magnetic field provided by the magnetic coils surrounding the arc discharge zone outside the reactor was used to produce acetylene from coal. The reactor, a schematic of which is shown in FIG. 2, is capable of operating at power inputs ranging from 50 Kw to 150 Kw. The reactor wall was constructed of a copper tube which was cooled by water circulating at high velocity in the annular gap between the copper tube and its external jacket.

Finely pulverized coal with a particle size distribution of 2% by weight in 6 microns range, 18% in 13 microns, 20% in 22.5 microns, 20% in 33 microns, 20% in 50 microns, 18% in 81 microns and 2% in 190 microns ranges were injected through the arc discharge zone with hydrogen as a carrier gas. The coal was a high volatile bituminous coal containing 38% by weight of volatile matters by proximate analysis. The ultimate analyses of the coal are as follows: (dry bases) 77.3% by weight carbon, 5.1% hydrogen, 8.4% oxygen, 1.4% nitrogen, 1.8% sulfur and 6.0% ash.

The reactor was operated at a subatmospheric pressure with the following input condition: power 148.8 Kw, coal 60 lb/hr, and hydrogen 27.7 standard cubic feet per minute (SCFM). The corresponding specific solid and gas enthalpies are, respectively, 2.5 Kw/lb coal per hour and 5.4 Kw/SCFM $H_2$. No active quench material was injected and the product stream was cooled through the water cooled reactor wall. The total residence time in both the reaction and cooling zones was approximately 5 milliseconds.

It is noted that a reactor of this configuration does not have a clear distinction between the reaction zone and the cooling zone as the cooling of the reaction stream starts as soon as the reaction commences. However, it is estimated by heat transfer calculations and energy balances that the reactor is about 75% energy efficient; i.e., 75% of the power input was taken up by the reagents and the balance by the reactor cooling water. The "net" specific solid and gas enthalpies were then 2.4 Kw/lb carbon per hour and 4.0 Kw/SCFM, and thus the input condition was situated just outside the envelope defined in FIG. 1.

The reactor output stream under this input condition contained 8.0% $C_2H_2$ by volume, and the acetylene yield was 17.5 lb. per 100 lb. of coal fed. The gross SER based on the power delivered at the electrodes was 14.2 Kwhr/lb $C_2H_2$.

EXAMPLE 2

The same reactor of Example 1 was operated with 60 Kw power, 63 lb. coal/hr. and 30 SCFM $H_2$. The corresponding gross specific solid and gas enthalpies were 0.95 Kw/lb. coal per hour and 2.0 Kw/SCFM $H_2$, and the "net" specific solid and gas enthalpies assuming 75% reactor energy efficiency were 0.92 Kw/lb carbon per hour and 1.5 Kw/SCFM $H_2$, respectively. Thus, the input condition lay just outside the lower left-hand boundary line of the envelope defined in FIG. 1.

The reactor output under this input condition was as follows: 7.8% by volume $C_2H_2$, an acetylene yield of 14.7 lb. $C_2H_2$/100 lb. coal fed, and an SER of 6.5 Kwhr/lb. $C_2H_2$.

EXAMPLE 3

The same reactor of Example 1 was operated with 73.4 Kw power, 63.0 lb coal/hr. and 27.5 SCFM $H_2$. The corresponding gross specific solid and gas enthalpies were 1.17 Kw/lb coal per hour and 2.67 Kw/SCFM $H_2$, and the "net" specific solid and gas enthalpies assuming a 75% reactor energy efficiency were 1.13 Kw/lb carbon per hour and 2.0 Kw/SCFM $H_2$. Thus, the input condition lay inside the envelope defined in FIG. 1.

The reactor output under this condition was as follows: acetylene concentration of 9.1% by volume, an acetylene yield of 23.6 lb $C_2H_2$/100 lb. coal fed, and an SER of 5.0 Kw/lb. $C_2H_2$.

EXAMPLE 4

The same reactor of Example 1 was operated with 88.0 Kw power, 93.1 lb. coal/hr. and 33.4 SCFM $H_2$. In this example, fine spray of water was injected six inches below the arc discharge zone, thus limiting the total reaction time to two milliseconds. The corresponding gross specific solid and gas enthalpies were 0.95 Kw/lb. coal per hour and 2.6 Kw/SCFM $H_2$, and the "net" reactor energy efficiency was 1.22 Kw/lb. carbon per hour and 1.98 Kw/SCFM $H_2$. Thus, the input condition lay inside the envelope defined in FIG. 1.

The reactor output under this condition was as follows: acetylene concentration of 9.2% by volume, an acetylene yield of 20.3 lb. $C_2H_2$/100 lb. coal fed, and an SER of 4.7 Kwhr/lb. $C_2H_2$.

Figure 5:
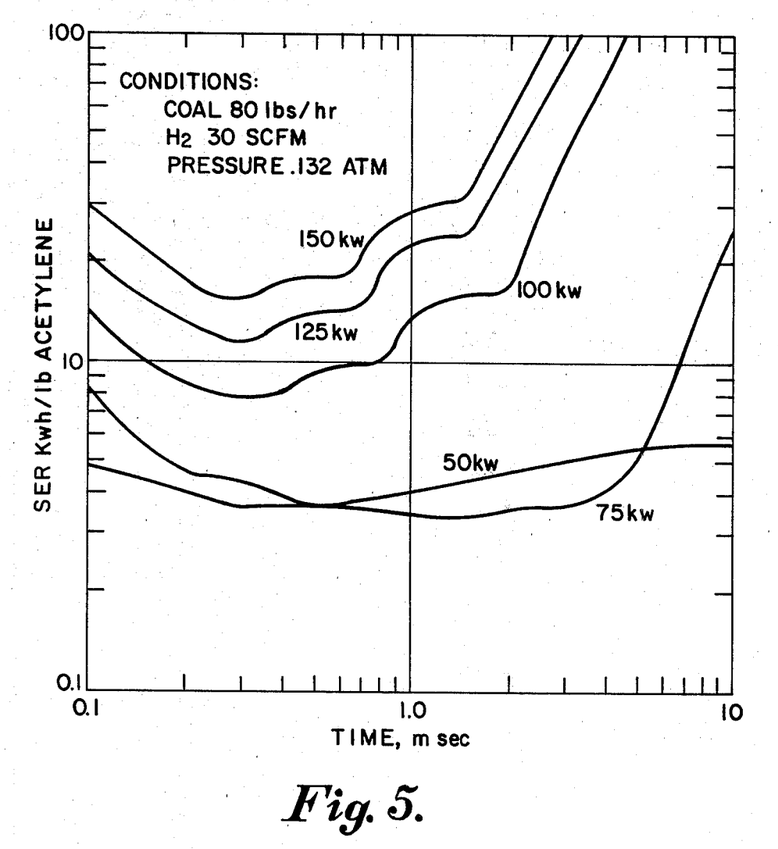
FIG. 5 is a curve of Specific Energy Requirement (SER) as a function of time.

FIG. 5 illustrates the effect of power variation on SER while hydrogen and coal feed rates are held constant at the experimentally-found optimum conditions. It is interesting to note that although the power input was varied from 50 to 150 Kw, the experimentally-detailed power input at 75 Kw gives the theoretical minimum SER. According to the model calculation for a hypothetical 100 percent energy-efficient reactor, calculated minimum SER is slightly below 3 Kw hours per pound acetylene and occurs in about 0.5 millisecond residence time.

In summary, therefore, the process of decomposing coal in high temperature hydrogen for producing acetylene turns out to be highly complex. Three operating parameters have been described for improving the yield of acetylene to reduce the specific energy required. These operating parameters, taken alone or in combination, were found through calculations and experimental data to be highly effective.

Taking into consideration the conditions shown in the envelope of FIG. 1, with the minimum SER points on the curves shown in FIG. 4 and the particle size distribution shown in FIG. 5, it is clear that the preferred residence time is from 0.5 to 5 milliseconds with a preferred range of particle sizes of 25 microns to about 50 microns.

The various features and advantages of the invention are thought to be clear from the foregoing description. Various other features and advantages not specifically enumerated will undoubtedly occur to those versed in the art, as likewise will many variations and modifications of the preferred embodiment illustrated, all of which may be achieved without departing from the spirit and scope of the invention as defined by the following claims:

I claim:

1. A method of producing acetylene from coal by decomposing coal in hydrogen:
   supplying coal particles and hydrogen at a predetermined controlled rate to a reaction zone;
   heating said coal and hydrogen so that the decomposition reaction takes place under conditions embraced by the area defined by the x, y coordinates (1.0, 2.5) (2.0, 2.5) (5.0, 1.5) (5.0, 0.6) (2.0, 0.6) (1.0, 1.25) where x coordinate is the specific gas enthalpy in Kw/SCFM $H_2$ and the y coordinate is the specific solid enthalpy in Kw/lb. carbon per Hr to produce acetylene; and
   removing said acetylene from the reaction zone to prevent it from decomposing.

2. A method of producing acetylene from coal by decomposing coal in hydrogen;
   supplying coal particles having a maximum diameter of 190 microns and hydrogen at a predetermined controlled rate to a reaction zone;
   heating said coal and hydrogen so that the decomposition reaction takes place under conditions embraced by the area defined by the x, y coordinates (1.0, 2.5) (2.0, 2.5) (5.0, 1.5) (5.0, 0.6) (2.0, 0.6) (1.0, 1.25) where x coordinate is the specific gas enthalpy in Kw/SCFM $H_2$ and the y coordinate is the specific solid enthalpy in Kw/lb carbon Hr to produce acetylene; and
   removing said acetylene from the reaction zone to prevent it from decomposing.

3. A process as defined in claim 2 where the preferred coal particle size is 25 to 50 microns and the preferred residence time of the coal and its decomposition products in the reaction zone is 0.5–5 milliseconds.

4. A process as defined in claim 3 where the solid particles are coal having an ASTM proximate volatile analysis of at least 18%.

5. A process as defined in claim 3 where the source of heat is an electric arc reactor.

6. A process as defined in claim 3 where the solid particles are coal having an ASTM proximate volatile analysis of at least 18% and the source of heat is an electric arc reactor.

7. A process as defined in claim 2 where the residence time of the coal and its decomposition products in the reaction zone is less than 10 milliseconds.

8. A method of producing acetylene from solid carbonaceous matter by decomposing the solid carbonaceous matter in gas:
   supplying solid carbonaceous matter particles and gas at a predetermined controlled rate to a reaction zone;
   heating said solid carbonaceous matter and gas so that the decomposition reaction takes place under conditions embraced by the area defined by the x, y coordinates (1.0, 2.5) (2.0, 2.5) (5.0, 1.5) (5.0, 0.6) (2.0, 0.6) (1.0, 1.25) where x coordinate is the specific gas enthalpy in Kw/SCFM gas and the y coordinate is the specific solid enthalpy in Kw/lb. carbon Hr to produce acetylene; and
   removing said acetylene from the reaction zone to prevent it from decomposing.

9. A method of producing acetylene from solid carbonaceous matter by decomposing the solid carbonaceous matter in gas;
   supplying solid carbonaceous matter particles having a maximum diameter of 190 microns and gas at a predetermined controlled rate to a reaction zone;
   heating said solid carbonaceous matter and gas so that the decomposition reaction takes place under conditions embraced by the area defined by the x, y coordinates (1.0, 2.5) (2.0, 2.5) (5.0, 1.5) (5.0, 0.6) (2.0, 0.6) (1.0, 1.25) where x coordinate is the specific gas enthalpy in Kw/SCFM gas and the y coordinate is the specific solid enthalpy in Kw/lb carbon per Hr to produce acetylene; and
   removing said acetylene from the reaction zone to prevent it from decomposing.

10. A process as defined in claim 9 where the preferred carbonaceous matter particle size is 25 to 50 microns and the preferred residence time of the carbonaceous matter and its decomposition products in the reaction zone is 0.5–5 milliseconds.

11. A process as defined in claim 9 where the residence time of the solid carbonaceous matter and its decomposition products in the reaction zone is less than 10 milliseconds.

12. A process as defined in claim 8 where gas comprises hydrogen.

13. A process as defined in claim 9 where the gas comprises hydrogen.

* * * * *